United States Patent [19]

Olesen

[11] 4,048,474

[45] Sept. 13, 1977

[54] METHOD AND APPARATUS FOR TIMING INTRAVENOUS LIQUID DRIP RATE

[76] Inventor: Ole V. Olesen, 615 Burley Road, Annapolis, Md. 21401

[21] Appl. No.: 648,882

[22] Filed: Jan. 14, 1976

[51] Int. Cl.² .................. G06F 15/42; H03K 3/78
[52] U.S. Cl. .................. 235/151.34; 128/214 E; 235/92 TF; 235/92 FQ; 328/39; 328/46
[58] Field of Search .............. 235/151.3, 151.34, 92 T, 235/92 TF, 92 FQ; 128/DIG. 3, 214 E, 214 F; 328/34, 39, 41, 42, 45, 46

[56] References Cited

U.S. PATENT DOCUMENTS

| | | | |
|---|---|---|---|
| 3,375,449 | 3/1968 | Ribour et al. | 328/46 |
| 3,832,640 | 8/1974 | Cederquist et al. | 328/34 |
| 3,894,389 | 7/1975 | Miura et al. | 235/92 T |
| 3,956,705 | 5/1976 | Mayer | 328/45 |
| 3,970,941 | 7/1976 | Leuschner | 328/46 |

*Primary Examiner*—Felix D. Gruber
*Attorney, Agent, or Firm*—Rose & Edell

[57] ABSTRACT

Accurate manual adjustment of a desired delivered flow rate in an intravenous liquid injection system is expedited and simplified. A programmable counter, fed by a pulse train of known repetition rate, is pre-set in accordance with the volume of liquid to be delivered, the size of the individual liquid drops, and the desired length of time during which the liquid is to be delivered. The counter provides a pulsed visible and/or audible indication at the drip rate determined by the pre-set conditions. The operator, upon comparison of the actual drip rate with the pulsed indication rate, can readily adjust the drip rate to coincide with the indications. The apparatus may include a pulse per unit time readout capability.

7 Claims, 3 Drawing Figures

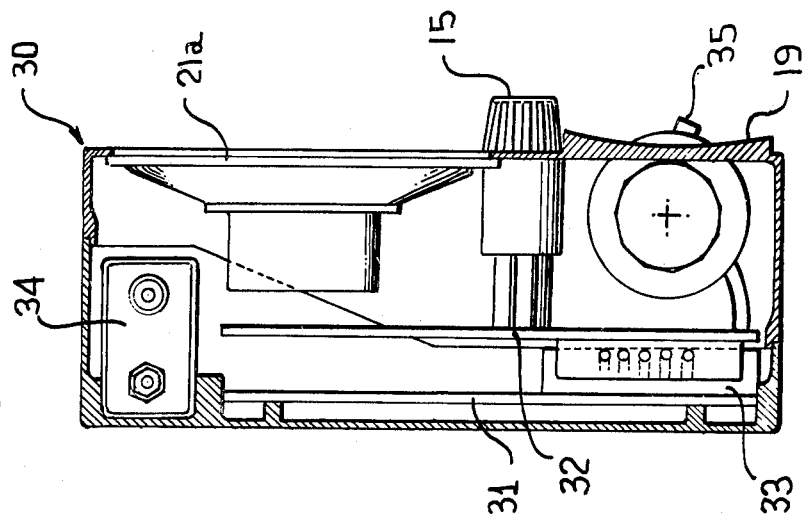
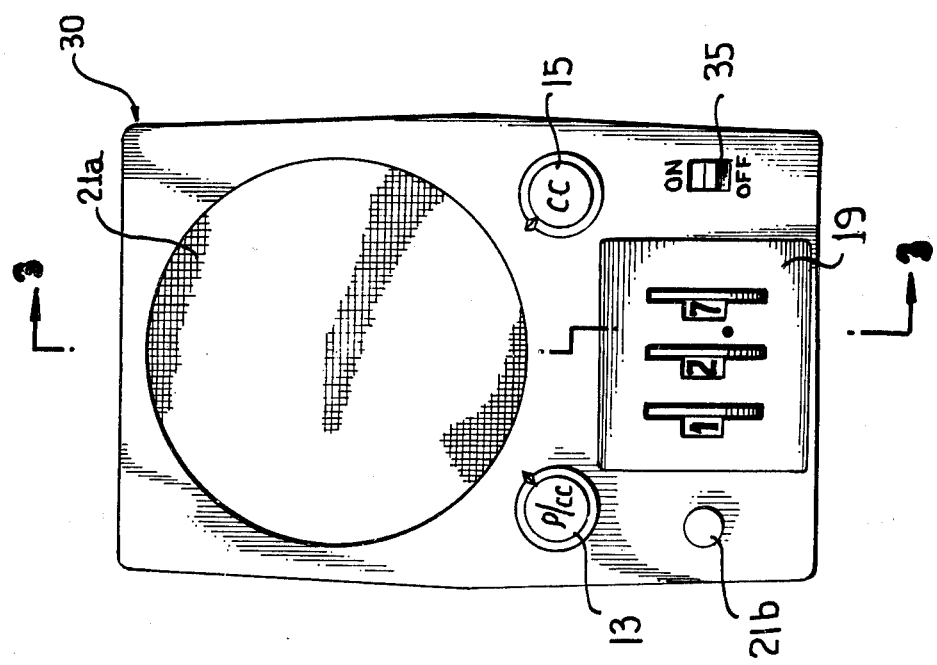

METHOD AND APPARATUS FOR TIMING INTRAVENOUS LIQUID DRIP RATE

BACKGROUND OF THE INVENTION

The present invention relates to improvements in systems for manually controlling the flow rate of intravenous liquid. More particularly, the present invention relates to a method and apparatus which permits a nurse or other hospital personnel to rapidly adjust a drip rate in an intravenous system to the desired rate without the need for costly and cumbersome automatic flow control devices.

It is the usual medical practice, when administering liquids intravenously, to employ an intravenous liquid injection system commonly referred to as an intravenous set. An intravenous set usually includes a bottle of the liquid to be delivered, a drip chamber, an intravenous feeding tube, and a suitable valve mechanism. The bottle is normally supported in an inverted position and includes a drop-forming member which delivers drops of the liquid into the drip chamber. The chamber in turn feeds the intravenous tube which is clamped to control the rate of intravenous liquid flow into the patient. The drip chamber serves the dual function of permitting a nurse or other attendant to observe the rate at which the liquid drops egress from the bottle, and creating a reservoir of the intravenous liquid at the lower end of the chamber to insure that no air enters the intravenous feeding tube leading to the patient. As is well understood by those skilled in the art, variations in the rate of liquid escape from the drip chamber to the feed tube control the back pressure in the drip chamber and thus govern the rate of formation of the drops egressing from the bottle. Thus, by changing the degree of clamping of the feed tube, the nurse or other attendant can control the drip rate from the bottle.

It has been the general practice in hospitals to have individuals periodically monitor the drop flow rate at each intravenous feeding station. Such monitoring of the drop flow rate is a tedious and time-consuming process which is prone to error and the possibility of serious consequences. In addition, a substantial reduction of the available time of qualified medical personnel is caused by the need to spend relatively long periods of time monitoring the drop flow rate. Typically, the nurse monitoring the drop flow rate employs a watch or clock to time the number of drops flowing from the bottle into the drip chamber during a given interval, usually one or more minutes. The nurse will then mentally perform the arithmetic computations necessary to convert the time and drop count into an appropriate parameter, for example, cubic centimeters per hour. If the calculated rate is substantially different than the prescribed rate, the nurse must manually adjust the clamp on the feed tube for a new rate, and then count the drops again and recalculate to measure the new rate. Clearly, each of the aforedescribed measurements and calculations and subsequent flow rate adjustments require several minutes time. Considering the number of stations being monitored, and the number of times per day each station must be monitored, it is apparent that a considerable portion of a nurse's time must be devoted to overseeing the delivery of intravenous liquid. In addition, under the pressure of heavy schedules, mental calculations performed by an overworked nurse may be incorrect, with the possibility of dangerous flow conditions developing.

It has been suggested in a multitude of prior art patents that the drop flow rate of intravenous liquid delivered to the patient may be automatically regulated by a suitable apparatus. Such apparatus usually employs a drop sensor which senses drops entering the drip chamber and which provides a signal from which the actual drip rate may be computed. Comparison circuitry for comparing this actual drip rate with a desired and pre-set drip rate is employed and in turn controls a mechanism such as a valve which regulates the flow through the intravenous feed tube leading to the patient. Such apparatus, in most cases, serves its intended function, namely: reducing the amount of time required by personnel to oversee the delivery of intravenous fluids to patients. However, such apparatus achieves the desired result at considerable cost. Since the apparatus cannot be time-shared for multiple concurrent use, if one hundred patients in a hospital require intravenous infusion of liquid concurrently, one hundred of these automatic control units must be available. The multiplied cost factor, for most hospitals, often outweighs the more efficient utilization of a nurse's time brought about by such units. Further, the complex electro-mechanical control arrangement is subject to failure which can have serious, and sometimes fatal, consequences.

It is an object of the present invention to provide an inexpensive approach to facilitating the manual adjustment of intravenous liquid flow rates without requiring long periods of time to make the necessary adjustments.

It is another object of the present invention to provide an apparatus which permits a nurse or other hospital attendant to easily and rapidly set the desired drip rate in an intravenous injection system.

It is another object of the present invention to provide a method for accurately, inexpensively, and quickly setting the desired drip rate in an intravenous set.

SUMMARY OF THE INVENTION

In accordance with the present invention a nurse or other hospital attendant carries with him/her a small timing device, no bigger than a miniaturized electronic calculator. The device is programmable to provide a series of audible and/or visible pulses at the prescribed drip rate for the intravenous liquid. The nurse or attendant need only compare the actual drip rate to the pulse indications emitted from the timer and adjust the feed tube clamp until the two rates coincide. The apparatus includes a source of clocked pulses having a known repetition rate and a programmable frequency divider arrangement. The frequency divider is programmed or pre-set in accordance with prescribed parameter conditions so that the overall frequency division ratio results in the desired drip rate frequency. The parameters employed for pre-setting the frequency divider include: drop size, volume of intravenous liquid to be delivered to the patient, and time interval during which a liquid is to be delivered. As an optional feature the apparatus may include a direct readout of pulsed indications provided per unit time, e.g. pulses per minute.

BRIEF DESCRIPTION OF THE DRAWINGS

The above and still further objects, features and advantages of the present invention will become apparent upon consideration of the following detailed description of one specific embodiment thereof, especially when taken in conjunction with the accompanying drawings, wherein:

FIG. 2 is a front view and plan of the preferred embodiment of the present invention; and FIG. 3 is a view in section through lines 3—3 of FIG. 2.

DESCRIPTION OF THE PREFERRED EMBODIMENTS

Figure 1:
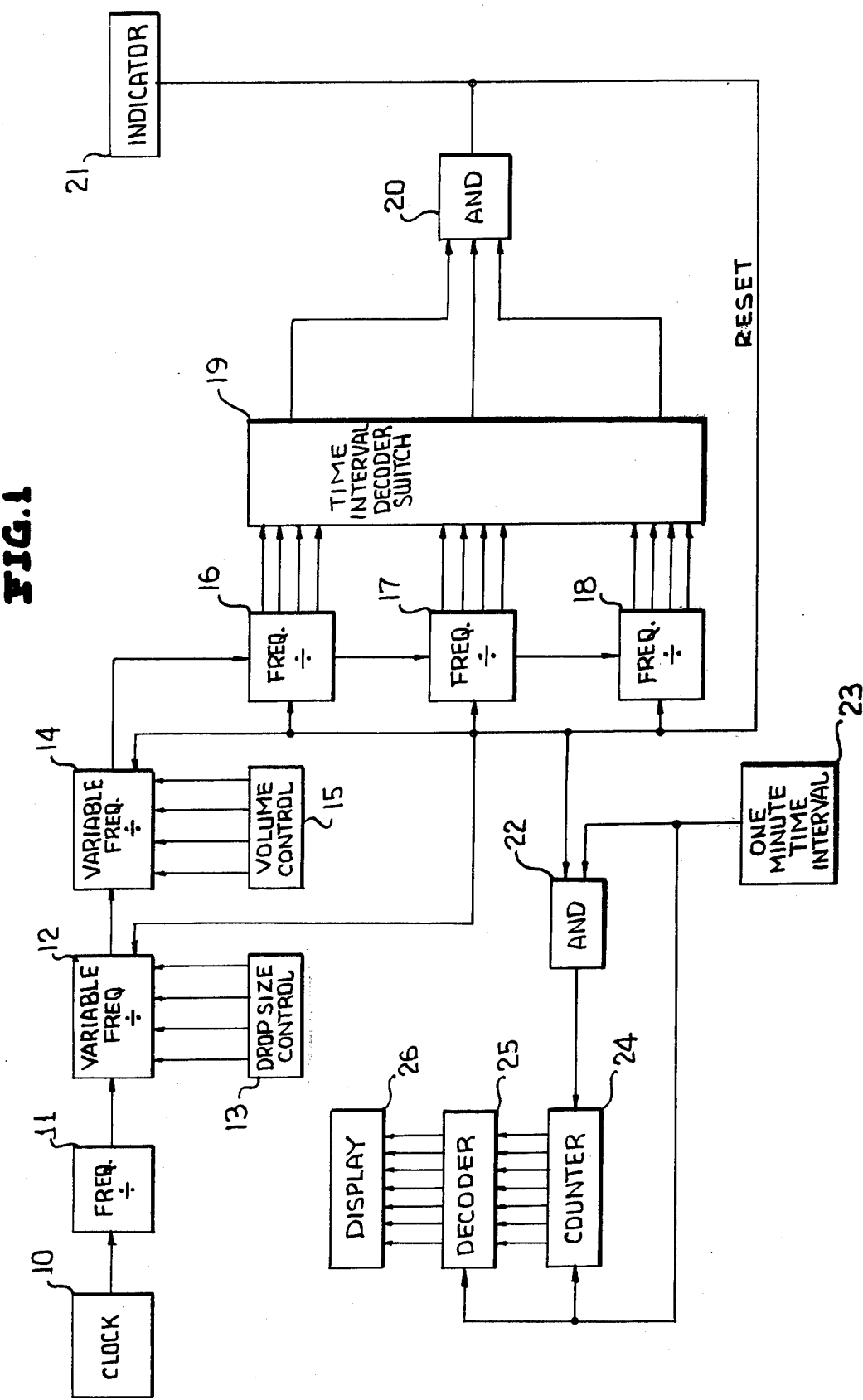
FIG. 1 is a schematic diagram of the preferred embodiment of the invention.

Referring specifically to the schematic diagram of FIG. 1, a clock pulse generator 10 delivers a train of clock pulses at a known repetition rate to a frequency divider 11. The frequency-divided pulse train provided by frequency divider 11 is applied to a variable frequency divider 12, the division ratio ($n$) of which is operator-adjustable by means of control unit 13. The output pulse train from variable frequency divider 12 is applied to a further variable frequency divider 14, the division ratio ($m$) of which is operator-adjustable by means of control unit 15. The pulse train provided by variable frequency divider 14 is delivered to frequency divider 16, the output train from which is delivered to frequency divider 17, the output pulse train from which is delivered to frequency divider 18. Frequency dividers 16, 17 and 18 divide by an integer and are connected to form respective decades of a three digit BCD counter. The output bits from frequency dividers 16, 17 and 18 are connected to an operator-controlled decoder switch 19. This decoder switch permits the operator to select any combination of the three decade digits represented by the frequency dividers 16, 17 and 18. When the count in these frequency dividers corresponds to that selected by the decoder switch 19, all three output lines from decoder switch 19 are at the logic 1 level and thereby activate AND gate 20. The output pulse from AND gate 20, which coincides with the time interval during which frequency dividers 16, 17 and 18 register the count selected by decoder switch 19, is applied to an indicator 21. Indicator 21 may be a lamp, a buzzer, or some other humanly-perceptible indicating device. In addition, the output pulse from AND gate 20 is applied as a reset signal to each of frequency dividers 12, 14, 16, 17 and 18.

The output pulse from AND gate 20 is also applied to AND gate 22 along with an output pulse from a 1-minute interval timer 23. The pulse from timer 23 enables AND gate 22 for one minute so that each of the pulses provided by AND gate 20 are passed through AND gate 22 during that minute and register counts accordingly at a binary counter 24. The count in counter 24 is decoded by a decoder 25 for purposes of feeding the count in suitable form to a digit display unit 26. The leading edge of the 1-minute timer output pulse resets both counter 24 and decoder 25 at the start of each counting interval.

As broadly indicated above, it is the function of the circuit of FIG. 1 to provide output pulses from AND gate 20 at a repetition rate which corresponds to a desired drip rate from an intravenous bottle into the drip chamber. These pulses each actuate indicator 21 so that the pulsed indications may be compared to the actual drip rate and the actual drip rate may be adjusted accordingly by the hospital attendant until it coincides with the pulsed indications. In order to achieve pulse indications at a desired drip rate, it is necessary that the pulse train by modified by the following parameters: (1) drop size; (2) total volume of intravenous liquid to be delivered to the patient; and (3) time interval over which the volume of intravenous liquid is to be delivered. Drop size is conventionally calibrated in terms of getts or drops per cubic centimeter; volume is conventionally calibrated in cubic centimeters; and the time interval is conventionally calibrated in tenths of hours. For purposes of the present discussion, these calibration factors shall be employed, it being understood that other units of calibration may be utilized for each of the parameters. Likewise, the order in which each calibration factor is applied to the pulse train may be varied from that described in the specific example mentioned below.

Control unit 13 is the drop size control unit. Typically the drop size control unit 13 includes a fourth-position switch which pre-sets different counts in variable frequency divider 12 in accordance with the setting of the switch. This technique is well known in the logic circuit field and a multitude of different commercially available circuits perform this function. Drop size is primarily a function of the drop-forming member or stem projecting from the intravenous bottle down toward the drip chamber and intravenous set. For a given drop-forming member the drop size remains relatively constant. Four standard drop sizes are employed in the usual intravenous equipment and for purposes of the present discussion the drop size control unit 13 will be considered to have a capability of selecting any one of those four sizes, namely: 10, 15, 20, and 60 drops per cubic centimeter. Drop size control unit 13 pre-sets variable frequency divider 12 in accordance with which of the drop sizes is selected by the operator. The pre-setting of variable frequency divider 12 by the drop size control unit 13 effects frequency division ratios ($n$) which are inversely relates to the drop size ratio. Thus, it may be desirable to have no frequency division for the 60 drops per cubic centimeter size, under which circumstances the pulse train from frequency divider 11 is passed directly through frequency divider 12 with no division effected. To achieve the proper ratios for the calibrated drop sizes, a division factor, $n=3$ would be necessary for the 20 drop per cubic centimeter size, a division ratio $n=4$ would be necessary for the 15 drops per cubic centimeter size, and a division ratio $n=6$ would be required for the 10 drops per cubic centimeter size. Naturally, these division ratios may be varied in proportion so that if a frequency division ratio $n=2$ is employed for the 60 drops per cubic centimeter drop size, division ratios of 6, 8 and 12 would be employed for the 20, 15 and 10 drops per cubic centimeter size, respectively.

The volume of liquid to be delivered intravenously to a patient is normally established by the size of the bottle utilized. That is, it is normal practice to select an intravenous bottle containing a volume of liquid, all of which is to be administered to the patient. These bottles typically come in standard sizes of 125, 250, 500 and 1,000 cubic centimeters. For purposes of the present discussion these four sizes are employed in calibrating the volume control unit 15; however, it is understood that other sizes may be calibrated in accordance with the same principles discussed herein. The frequency division ratios employed to calibrate for these various volumes vary inversely with the volumes themselves. Thus, for example, if a frequency division ratio $m=2$ is effected at variable frequency divider 14 by the volume control unit 15 in order to achieve a setting for 1,000 cubic centimeters, division ratios of 4, 8, and 16 are utilized to achieve settings for 500, 250 and 125 cubic centimeters, respectively. Again, these frequency division ratios may be varied in fixed proportion to one another.

It is to be understood that the description set forth above with respect to achieving variable frequency division ratios in frequency dividers 12 and 14 assumes that a technique of pre-setting counts into the frequency divider is employed to achieve different ratios. It should be noted that, depending upon the nature of the frequency divider utilized, other approaches to selecting a frequency division factor may be more suitable. For example, a simple selector switch connected at the output line of the frequency divider and switchable to the output stage of any one or more appropriately connected bits is a similarly suitable approach. The important point, in any case, is that any technique may be employed to achieve the desired frequency division ratios under operator selection.

Frequency dividers 16, 17 and 18 are each 4 bit counters representing a particular decade in a 3 digit binary coded decimal counter. Divider 16 represents tenths of hours, divider 17 represents hours, and divider 18 represents ten hours. The time interval decoder switch 19 may in fact be three individual switches, each having ten positions which respond to the 4 output bits of its associated frequency divider to provide an output signal only when those 4 bits correspond to a selected decimal number. Switches such as these are availabe from numerous manufacturers. The simplest approach to calibrating the repetition rate in accordance with the desired time interval for delivery of intravenous liquid is to divide directly by the number selected by the time interval decoder switch 19. For example, if it is desired to deliver all of the intravenous liquid to the patient within a 30 minute interval (0.5 hours), the time interval switches effect a division of 5 when placed in the 00.5 positions. Thus when a count of 5 is present in frequency divider 16 and the counts of 0 are present in frequency dividers 17 and 18 the three output lines from the time interval decoder switch 19 will be binary 1 simultaneously, and therefore AND gate 20 will be enabled to provide a pulse indication from indicator 21. Likewise, if a 24 hour time interval is selected, a frequency division ratio of 240 is utilized so that a count of 0 in frequency divider 16, a count of 4 in frequency divider 17 and a count of 2 in frequency divider 18 define the condition upon which AND gate 20 will be enabled.

In order to facilitate an understanding of the concept of the present invention as thus far described, a few examples shall be given. In each of these examples it is assumed that the repetition rate of clock pulses provided by the clock pulse source 10 is 3.33 KHz, and that the frequency divider 11 has a frequency division ratio of ten, so that the pulse repetition rate of the train delivered to variable frequency divider 12 is 333 Hz. In the first example it is assumed that 1,000 cubic centimeters of intravenous liquid is to be delivered over a 24 hour interval with a drop size of 60 drops per cubic centimeter. The drop size control unit 13 is thus set to the 60 drops per cubic centimeter position in which case, for purposes of the present example, it is assumed that no frequency division occurs and that the pulse train feeds through the variable frequency divider 12 with no effect on its repetition rate. The volume control unit 15 is set at the 1,000 cubic centimeter position which, for purposes of the present discussion, is assumed to effect a division ratio $m=2$. Therefore, the repetition rate of pulses delivered to frequency divider 16 is 167 Hz. The 24 hour time interval chosen for the example requires that a division factor of 240 be effected at the frequency dividers 16, 17 and 18. Under such circumstances, the repetition rate of pulses provided by AND gate 20 to indicator 21 is approximately 0.7 pulses per second or 42 pulses per minute. The hospital attendant assigned to adjust the intravenous delivery rate would modify the position of the clamp on the intravenous delivery tube until the drip rate into the drip chamber coincides with the pulse rate of the visible and/or audible indictor 21. As a second example let it be assumed that 500 cubic centimeters of intravenous liquid are to be delivered over a 12 hour interval and that the drop size for the mechanism employed is 20 drops per cubic centimeter. The drop size control unit 13 is set at position 20, the volume control unit 15 is set at the 500 cubic centimeter position, and the time interval decoder switch is set at 12.0. Consistent with the calibration factors utilized in the first example, a 20 drops per cubic centimeter setting at the drop size control unit 13 effects a frequency division ratio $n=3$. Thus, the 333 Hz. pulse train applied to variable frequency divider 12 results in a 111 Hz. pulse train applied to variable frequency divider 14. The frequency division ratio established by the 500 cubic centimeter setting at volume control unit 15 is $m=4$ so that the 111 Hz. pulse train applied to frequency divider 14 results in a 27.75 Hz. pulse train applied to frequency divider 16. The frequency division ratio for the 12.0 hours setting at time interval decoder switch 19 results in a frequency division ratio of 120 so that the 27.75 Hz. pulse train is further divided by frequency dividers 16, 17 and 18 and the pulse rate at the output of AND gate 20 is approximately 0.23 Hz. or 13.8 pulses per minute. Again, the hospital attendant would observe or listen to the pulsed indications from indicator 21 and adjust the clamp on the intravenous feed tube accordingly so that the pulses into the drip chamber achieve a rate which corresponds to the indicator pulse rate.

In each of the examples described above it is noted that counters 12, 14, 16, 17 and 18 are re-set with each output pulses from AND gate 20 so that each begins the next count series in its re-set state. It should also be noted that frequency divider 11 may be dispensed with, depending upon the frequency of pulses delivered by clock pulse source 10 and by the particular division ratios utilized for the settings of drop size control 13 and volume control 15. For example, if clock pulse source 10 provides a pulse train at 6.66 pulses per second, frequency divider 11 may be utilized with a division ratio of 20; alternatively the division ratio of frequency divider 11 may remain 10 and the four division ratios employed at frequency divider 12 in response to the four settings of control unit 13 may be 2, 6, 8 and 12; alternatively, the frequency division ratios of frequency dividers 11 and 12 may remain the same as described in the aforementioned examples and the four settable frequency division ratios at frequency divider 14 may be 4, 8, 16 and 32. It is evident that the permutations and the combinations of the settings of the frequency divider division ratios and the clock pulse freqency are substantially infinite, the only limitation being that the pulse rate of indicator 21, for the particular parameters employed, be such that all of the prescribed volume of intravenous liquid be administered within the prescribed time interval.

It is evident that the invention as thus far described permits a considerable time saving for the hospital attendant who, instead of having to count drips into the drip chamber for 1 or more minutes and then make mental calculations to determine whether the drip rate is proper, need merely adjust the drip rate to coincide with the pulsed indications. No trial and error mental calculations are reqired and the attendant can oversee multiple intravenous sets in a small fraction of the time previously required. On the other hand, the device is portable, being nominally of the same size as a miniature pocket calculator. Consequently, the attendant may carry the unit with him or her from patient to patient so that substantially fewer units are required than would be the case if a permanently installed positive flow control device were utilized.

Elements 22, 23, 24, 25 and 26 constitute an optional feature associated with the present invention. More specifically, these elements permit a digital display of the number of pulses per unit time, preferably pulses per minute being provided by AND gate 20. This feature has a number of advantages including that which derives from the conditions when a doctor prescribes the actual drip rate rather than the time interval over which the intravenous liquid is to be delivered. Thus, if a physician prescribes a predetermined volume of intravenous liquid to be delivered at a drip rate of 30 drops per minute, the attendant would set the volume control unit 15 for that volume, and also set the drop size control unit 13 for the drop size appropriate to the drop forming stem in the bottle employed. The attendant would then adjust the settings on the time interval decoder switch 19 until the display at display unit 26 corrsponds in pulses per minute to the drip rate prescribed by the physician.

Referring specifically to FIGS. 2 and 3 of the accompanying drawings, the construction of a unit embodying the principles described in relation to FIG. 1 may be observed. A small housing 30 contains all of the components 10 through 21. The housing is in the form of a rectangular block and may be as small as 4 inches in height, 2⅜ inches in width, and 1¾ inches in depth. As will be noted this housing is as small or smaller than a miniature pocket calculator and can be readily carried from patient to patient by a hospital attendant. Electronic circuit components designated generally by the numeral 33, are mounted on printed circuit boards 31 and 32. Power for the circuitry is supplied by a battery 34. The drop size control 13, the volume control 15 and the time interval decoder unit 19 are mounted on the front panel, each of these controls being associated with an appropriate calibration position corresponding to the various settings of the control. An on-off switch 35 controls application of power from the battery 34 to the circuitry. A small loud speaker 21a provides audible pulses in response to the pulses provided by AND gate 20 of FIG. 1. Alternatively, or additionally, a lamp 21b pulses on and off at the same pulse rate.

The particular packaging illustrated in FIGS. 2 and 3 is by no means limiting on the present invention. The purpose for showing such packaging at all is to illustrate that the unit according to the pesent invention can be housed in a very small, easily portable package in a manner which facilitates its use.

While I have described and illustrated one specific embodiment of my invention, it will be clear that variations of the details of construction which are specifically illustrated and described may be resorted to without departing from the true spirit and scope of the invention as defined in the appended claims.

I claim:

1. Electronic apparatus for monitoring the rate of drop flow of liquid into the drip chamber of an intravenous set, said apparatus comprising:
   means for providing a train of clock pulses at a known pulse frequency;
   programmable frequency divider means connected to receive and count pulses in said pulse train and provide an output pulse after a controllable number of pulses from said pulse train have been counted, said controllable number being selectively variable;
   first operator-controlled means, connected to said programmable frequency divider means and calibrated in drops per unit volume of liquid, for selectively varying said controllable number;
   second operator-controlled means connected to said programmable frequency divider means and calibrated in volume, for selectively varying said controllable number;
   third operator-controlled means, connected to said programmable frequency divider means and calibrated in time, for selectively varying said controllable number; and
   indicator means, connected to receive each output pulse from said programmable frequency divider means, for providing a momentary indication in response to each said output pulse;
   whereby, upon setting said first means to correspond to the desired drop size, the second means to correspond to a specified quantity of liquid to be delivered, and the third means to correspond to the desired time period over which said specified quantity of liquid is to be delivered, an operator can compare the repetition rate of said momentary indication with said rate of drop flow of liquid and adjust the latter as desired.

2. The apparatus according to claim 1:
   wherein said programmable frequency divider means comprises:
   a first frequency divider having an adjustable frequency division factor;
   a second frequency divider having an adjustable frequency division factor;
   a third freeqency divider having an adjustable frequency division factor; and
   means connecting said first, second and third freqency dividers in cascade to successively divide the repetition rate of said train of clock pulses and provide said output pulse after each complete freqquency division cycle;
   and wherein said first, second and third control means are connected to vary the frequency division factor of said first, second and third frequency dividers, respectively.

3. The apparatus according to claim 1 wherein:
   said first control means is calibrated in drops per cubic centimeter;
   said second control means is calibrated in cubic centimeters; and
   said third control means is calibrated in tenths of hours.

4. The apparatus according to claim 1 further comprising means for providing a visual display of number of said output pulses provided per minute by said programmable frequency divider means.

5. Electronic timing apparatus for providing a humanly perceptible pulsed indication at selectively variable repetition rates for comparison to the drip flow rate in an intravenous set, said apparatus comprising:

clock means for providing a train of pulses at a known frequency;

a first freqency divider, having a selectively variable frequency division ratio $n$, connected to receive and frequency-divide said train of pulses and provide one output pulse for each $n$ pulses in said pulse train;

first operator-actuable means, calibrated in intravenous liquid drop size, for selectively varying value of $n$;

a second frequency divider, having a selectively variable frequency division ratio $m$, connected to receive and frequency-divide output pulses from said first frequency divider and provide one output pulse for each $m$ pulses received;

second operator-actuable means, calibrated in total volume of intravenous liquid to be administered, for selectively varying the value of $m$;

a third frequency divider arranged to receive and count output pulses from said second frequency divider;

third operator-actuable means, calibrated in units of time, for providing an output pulse when the pulse count in said third frequency divider achieves an operator-selectable number;

indicator means for providing said humanly perceptible pulsed indication in response to each output pulse from said third operator-controlled means; and reset means for resetting said first, second and third frequency dividers in response to each output pulse from said third operator-actuable means where $m$, $n$ are integers.

6. The apparatus according to claim 5 further comprising:

display means responsive to output pulses from said third operator-actuable means for providing a display of the number of such pulses provided per minute.

7. The apparatus according to claim 5:

wherein said clock pulses received by said first frequency divider have a repetition rate of 333 pulses per second;

wherein said first operator-actuable means is capable of selecting one, three, four and six for values of $n$ corresponding to drop size values of 60, 20, 15 and 10 drops per cubic centimeter, respectively;

wherein said second operator-actuable means is capable of selecting two, four, six and eight for values $m$ corresponding to liquid volume values of 1,000, 500, 250 and 125 cubic centimeteres, respectively; and wherein said third operator-actuable means is calibrated one tenth of an hour per count in said third frequency divider.

* * * * *